(12) United States Patent
Oomori et al.

(10) Patent No.: US 6,271,397 B1
(45) Date of Patent: Aug. 7, 2001

(54) L-ASCORBIC ACID-2-PHOSPHORIC ACID POTASSIUM CRYSTAL AND METHOD FOR PRODUCING THE SAME

(75) Inventors: Kazuhiro Oomori, Chiba; Yuji Kobayashi; Takamitsu Utsukihara, both of Kanagawa; Sumio Soya, Tokyo, all of (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/326,696

(22) Filed: Jun. 7, 1999

Related U.S. Application Data
(60) Provisional application No. 60/114,162, filed on Dec. 29, 1998.

(30) Foreign Application Priority Data

Jun. 5, 1998 (JP) .................................................. 10-174080

(51) Int. Cl.$^7$ ...................................................... C07F 9/06
(52) U.S. Cl. .......................................... 549/222; 549/218
(58) Field of Search ..................................... 549/222, 218

(56) References Cited

U.S. PATENT DOCUMENTS

| | | | |
|---|---|---|---|
| 3,671,549 | * | 6/1972 | Hinkley . |
| 5,202,445 | * | 4/1993 | Dobler ................................. 549/315 |
| 5,420,302 | | 5/1995 | Kaiser et al. . |
| 5,516,919 | * | 5/1996 | Sano et al. ........................... 549/222 |

FOREIGN PATENT DOCUMENTS

| | | |
|---|---|---|
| 0 508 233 A2 | 10/1992 | (EP) . |
| 0 679 655 A2 | 11/1995 | (EP) . |

OTHER PUBLICATIONS

CA:110:160221 abs of JP62298508, Jun. 1986.*
CA:111:12539 abs of NL 8700518, Oct. 1988.*
H. Nomura et al., "X–Ray Analysis of L–Ascorbic Acid 2–0–Phosphate", *Chemical and Pharmaceutical Bulletin*, vol. 30, No. 3, pp. 1024–1029, Mar. 3, 1982.

* cited by examiner

*Primary Examiner*—Jean F. Vollano
(74) *Attorney, Agent, or Firm*—Sughrue, Mion, Zinn, Macpeak & Seas, PLLC

(57) ABSTRACT

A high-purity L-ascorbic acid-2-phosphoric acid potassium crystal having excellent stability, and a method for simply producing the high-purity L-ascorbic acid-2-phosphoric acid potassium in a high yield by adding dropwise a solution containing L-ascorbic acid-2-phosphoric potassium to methanol or simultaneously mixing methanol and a solution containing L-ascorbic acid-2-phosphoric acid potassium. By the production method of the present invention, high-purity L-ascorbic acid-2-phosphoric acid potassium crystal having excellent stability can be simply produced in a high yield. The L-ascorbic acid-2-phosphoric acid potassium crystal obtained by the production method of the present invention is used for feedstuff, cosmetic materials, medical products, food additive and the like.

3 Claims, 3 Drawing Sheets

×1K

High Resolution SEM Photograph

× 4 K

High Resolution SEM Photograph

L-ASCORBIC ACID-2-PHOSPHORIC ACID POTASSIUM CRYSTAL AND METHOD FOR PRODUCING THE SAME

CROSS REFERENCE TO RELATED APPLICATIONS

This application is an application filed under 35 U.S.C. §111(a) claiming benefit pursuant to 35 U.S.C. §119(e)(i) of the filing date of the Provisional Application No. 60/114,162 filed Dec. 29, 1998 pursuant to 35 U.S.C. §111(b).

FIELD OF THE INVENTION

The present invention relates to L-ascorbic acid-2-phosphoric acid potassium crystal (hereinafter "L-ascorbic acid-2-phosphoric acid potassium" is sometimes simply referred to as "APK") and a method for producing the APK crystal, particularly high-purity APK crystal.

High-purity APK crystal is useful as a stabilized derivative of L-ascorbic acid and can be used in various industrial fields such as cosmetic materials, medical products, food additives and feedstuff.

BACKGROUND OF THE INVENTION

L-Ascorbic acid (vitamin C) is known to have diverse physiological actions and pharmacological actions and particularly by virtue of its effect of preventing deposition of melamine dye, L-ascorbic acid has been used in whitening cosmetics. However, L-ascorbic acid is unstable to oxygen or heat and has heretofore been formed into a derivative stabilized against oxygen or heat by converting the hydroxyl group at the 2-position of L-ascorbic acid into a phosphoric acid ester. A salt, particularly a magnesium salt of L-ascorbic acid-2-phosphoric acid ester (hereinafter "L-ascorbic acid-2-phosphoric acid magnesium" is sometimes simply referred to as "APM") is being used as a stabilized vitamin C derivative.

The currently used APM occasionally deposits during the storage of a cosmetic material and causes the problem of a rough feeling on use of the cosmetic material. In order to prevent deposition of APM, an organic acid such as citric acid or an amino acid such as glycine is added, however, deposition cannot be completely prevented. Thus, a stabilized vitamin C derivative free of deposition in a cosmetic material, particularly, APK having a high solubility in water is demanded.

Conventionally, APK has a very high solubility in water, and in turn it has not been possible to obtain APK crystals. As such, very few publications on the properties of APK crystal, such as melting point (decomposition point), exist. Furthermore, almost no production method is known for the formation of APK powder. Merely, reports on L-ascorbic acid-2-phosphoric acid ester (hereinafter "L-ascorbic acid-2-phosphoric acid ester" is sometimes simply referred to as "2-AP") partly refer to the APK powder.

For example, JP-A-59-51293 (the term "JP-A" as used herein means an "unexamined published Japanese patent application") describes a method for purifying 2-AP using activated carbon, where it is stated that after decationization, 2-AP is preferably formed into a salt such as the magnesium salt, calcium salt, sodium salt or potassium salt, and further that the product obtained is subjected to usual processes such as condensation and crystallization to obtain a product almost free of coloring. However, the salt used in all Examples is the magnesium salt and the potassium salt is not described at all. The present inventors have attempted to isolate the potassium salt by the method described in this Japanese patent publication, however, APK crystal could not be isolated and only a glutinous and partly agar-like product was obtained.

JP-A-8-12693 describes the production of APK in more detail, where a solution containing APK is concentrated to an APK concentration of about 10% and the crystals precipitated are collected by filtration and dried at room temperature to obtain APK. The present inventors faithfully repeated this method to isolate crystallized APK, however, crystallized APK could not be isolated and only a glutinous and partly agar-like product was obtained. In this Japanese patent publication, methanol, ethanol, propanol, acetone and the like are described as examples of water-soluble solvents for crystallizing APK. Accordingly, the present inventors attempted to isolate crystallized APK by the method of this Japanese patent publication using these water-soluble solvents individually or as a mixture, however, only a glutinous and partly agar-like product was obtained.

The glutinous APK obtained by these methods has a very high solubility in water of about 50% (wt/V). A cosmetic material produced using this glutinous APK exhibits excellent storage stability, for example, even when a lotion produced using such a glutinous APK is stored in at room temperature or 40° C. for 8 months, APK was not deposited. However, the glutinous APK has low purity. Moreover, due to its high viscosity, APK adheres to the container on handling such as weighing or charging and this results in a great loss and is not profitable.

As described in the foregoing, APK is difficult to obtain as a crystal and therefore, use thereof has been heretofore limited despite its extremely high solubility in water and remarkably high stability in cosmetic materials. Thus, APK crystals easy to handle are needed.

The present invention provides a novel APK crystal with reduced coloring and also provides a method for simply producing APK as a crystal in high yield.

As a result of extensive investigations to overcome the above-described problems, the present inventors have surprisingly found that when methanol is used and a solution containing APK is added to the methanol or methanol and a solution containing APK are simultaneously mixed, such that methanol substantially accounts for 30% (V/V) or more of the sum of the solution and methanol, APK can be easily crystallized in a high yield, and further that the APK crystals obtained have remarkable stability in cosmetic materials. The present invention has been accomplished based on these findings.

SUMMARY OF THE INVENTION

The present invention provides a method for producing APK comprising adding an APK-containing solution to methanol at a temperature of from −30 to 80° C. preferably over 0.5 hour such that the methanol concentration in the solution becomes from 30 to 95% (V/V) at the completion of addition and thereby APK is crystallized, or a method for producing APK comprising simultaneously mixing methanol and an APK-containing solution at a temperature of from −30 to 80° C. such that methanol substantially always accounts for from 30 to 95% (V/V) of the sum of the solution and methanol and thereby APK is crystallized.

The production method of the present invention comprises adding a solution containing APK is added to methanol or methanol and a solution containing APK are simultaneously mixed. In this case, it is necessary to substantially maintain the condition such that methanol is always present in a concentration of 30% (V/V) or more. In the case of producing the APK crystal of the present invention in a batch system, a method of dropwise adding a solution containing APK to methanol may be used, and in the case of producing the APK in a continuous system, a method of simultaneously mixing methanol and a solution containing APK may be used.

The present invention provides a APK crystal having a molecular formula: $C_6H_6O_9PK_3 \cdot H_2O$. Furthermore, the present invention provides a APK crystal obtainable by producing according to the above-described production method.

DESCRIPTION OF THE PREFERRED EMBODIMENTS

Figure 1:
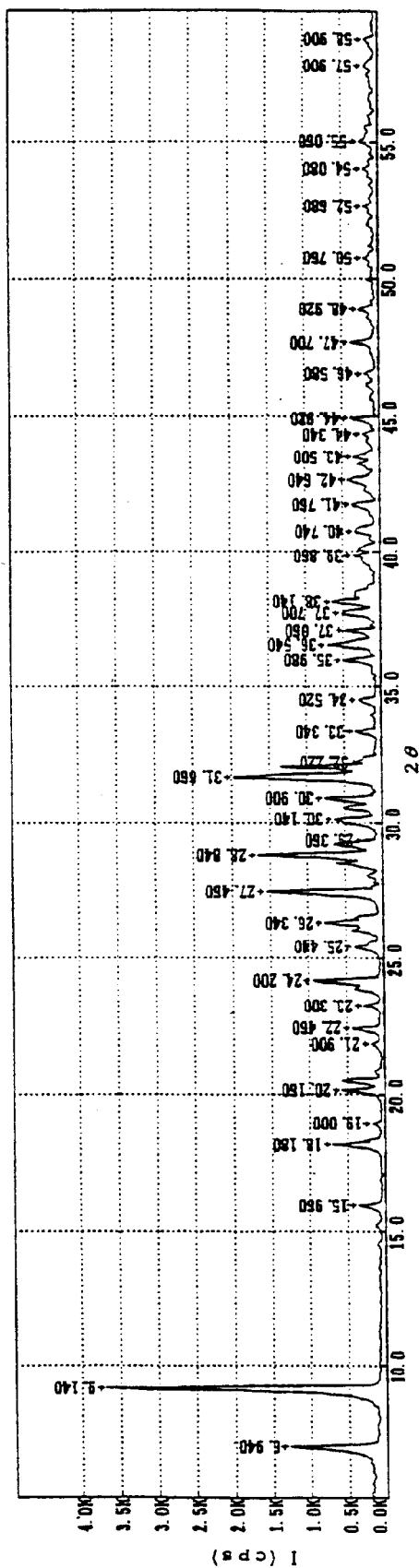
FIG. 1 is an X-ray diffraction spectrum (CuKα ray, 30 kV, 100 mA) of L-ascorbic acid-2-phosphoric acid potassium crystal obtained according to the present invention, where the ordinate indicates the diffraction intensity (unit: count/sec) and the abscissa indicates the diffraction angle (unit: 2θ (°)).

In general, when a water-soluble solvent is added dropwise to a solution containing APK, the APK precipitated is glutinous and partly agar-like but does not form powder even if it is added at −30 to 80° C. Accordingly, after the water-soluble solvent is removed, for example, by decantation, the APK collected is glutinous. The glutinous APK is highly viscous and a great loss is incurred at the time of collection. Furthermore, many impurities are mixed therein and the purity is low. The "water-soluble solvent" used herein is, for example, a lower aliphatic alcohol having 4 or less carbon atoms, an aliphatic saturated ketone having 4 or less carbon atoms or a cyclic ether having 5 or less carbon atoms. Even if these solvents are used individually or as a mixture, APK crystal cannot be obtained but only glutinous and partly agar-like APK is obtained.

However, according to the present invention, a solution containing APK is added, optionally dropwise, to methanol as a water-soluble solvent or methanol and a solution containing APK are simultaneously mixed, at a temperature condition of from −30 to 80° C., preferably from room temperature to 70° C., and thereby APK crystals can be simply isolated in a high yield without producing APK which is glutinous or agar-like. The amount of methanol used here is a high concentration, preferably 90% (in V/V) or more. When APK is contacted with methanol at high concentration, by virtue of excellent dehydration action of the methanol, supersaturation is rapidly avoided, as a result, the APK can be crystallized without becoming glutinous or agar-like.

The solution containing APK for use in the production method of the present invention may be any of a 2-AP solution and a 2-AP metal salt solution or alkaline earth metal salt solution so long as it contains 2-AP. For example, a 2-AP-containing solution obtained by directly phosphorylating ascorbic acid may be used (see, JP-B-43-9219 (the term "JP-B" as used herein means an "examined Japanese patent publication"), JP-B-45-23746 and JP-A-6-345786). Also, a 2-AP-containing solution obtained by phosphorylating 5,6-O-isopropylidene-L-ascorbic acid may be suitably used (see, JP-B-43-9219, JP-B-45-4497, JP-B-45-30328, JP-B-59-4438). Furthermore, a 2-AP-containing solution produced from L-ascorbic acid and a phosphoric acid donor using the action of an enzyme or microbe may also be used (see, JP-A-2-42996). Examples of the metal salt include the sodium salt and potassium salt. Examples of the alkaline earth metal salt include the magnesium salt and calcium salt.

In the case where 2-AP is in the form of a salt or where the 2-AP-containing solution contains an alkali metal or alkaline earth metal, the aqueous solution thereof is preferably decationized by treating it with an appropriate ion exchange resin. First, 2-AP is adsorbed to an ion exchange resin and eluted with diluted hydrochloric acid of from 0.1 to 2N. Then, the pH is adjusted with potassium hydroxide.

The pH adjustment with potassium hydroxide is usually performed using an aqueous potassium hydroxide solution in a concentration of from 10 to 48%. The pH is adjusted to from 7 to 11, and in view of the third equivalence point of 2-AP, the pH is preferably adjusted to from 9 to 10.

The APK concentration in the solution after the pH adjustment is from 1 to 30% (wt/v), preferably from 5 to 15% (wt/v). If desired, the solution is diluted with water or concentrated by heating, decompression, reverse osmosis membrane or the like. A water-soluble solvent may be mixed in the APK-containing solution, however, the amount of the solvent mixed is limited to the range of not causing separation of APK in the APK-containing solution.

Subsequently, the APK-containing solution is added dropwise to methanol such that the metal concentration after the crystallization falls within the range of from 30 to 95% (V/V), preferably from 70 to 90% (V/V), or methanol and the APK-containing solution are mixed by simultaneously feeding them such that the methanol concentration after the mixing falls within the range of from 30 to 95% (V/V), preferably from 70 to 90% (V/V). The methanol used here is more advantageous as the purity is higher and preferably has a purity of 90% or more in general. Accordingly, methanol having a purity of from 90 to 95% is suitably used. In the production of this APK, the presence of a seed crystal is not necessarily essential, however, a seed crystal may be added if desired.

In the production method of the present invention, methanol must be used. If a water-soluble solvent, for example, a lower aliphatic alcohol having 4 or less carbon atoms such as ethanol or isopropyl alcohol, an aliphatic saturated ketone having 4 or less carbon atoms such as acetone, or a cyclic ether such as tetrahydrofuran or 1,4-dioxane is used, APK can be hardly obtained as a powder in the production method of the present invention. If ethanol which is the same lower aliphatic alcohol as methanol is used, APK may partially form powder but the greater part of APK is glutinous and precipitates on the container bottom. This seems to occur because methanol has excellent dehydration action as compared with other water-soluble solvents.

In usual, the APK-containing solution is added dropwise to methanol or these are simultaneously mixed, at a temperature of from −30 to 80° C. If the temperature is less than −30° C., the methanol disadvantageously freezes depending on the methanol concentration after the dropwise addition or mixing. If the temperature exceeds 80° C., the crystallization of APK is not affected at all but since the temperature is higher than the boiling point of methanol, the efficiency in recovery of methanol which has evaporated decreases. Accordingly, the temperature at the dropwise addition or mixing is preferably from room temperature to 70° C.

The time spent for the dropwise addition of an APK-containing solution to methanol or the mixing of methanol and an APK-containing solution by simultaneously feeding these may be 0.5 hour or more. If the dropwise addition rate is too fast, the APK crystals precipitated have a small particle size and pass through a sieve at the separation and collection in a centrifugal separator, as a result, the recovery decreases. If the dropwise addition rate is slow, there arises no problem arises with respect to the recovery as well as the coloring but the plant is operated needlessly and this is disadvantageous from the standpoint of profitability. Accordingly, the dropwise addition is preferably performed over from 1 to 10 hours.

After an APK-containing solution is added dropwise to methanol or methanol and an APK-containing solution are simultaneously fed and mixed, the resulting mixture is ripened for from 0.25 to 1 hour. Thereafter, APK crystals are isolated using an apparatus such as centrifugal separator, thoroughly washed with methanol and then subjected to treatments such as vacuum drying. After that, white APK crystals having a high purity can be obtained in a high yield.

The composition and physicochemical properties of each APK crystal obtained according to the present invention are shown in Table 1.

(1) Elemental Analysis:

TABLE 1

|   |   | Calculated for $C_6H_6O_9PK_3 \cdot H_2O$ | Found (%) |
|---|---|---|---|
| C | Elemental analysis method | 18.56 | 18.49 |
| H |   | 1.56 | 1.62 |
| P | atomic absorption method | 7.98 | 7.90 |
| K | atomic absorption method | 30.20 | 30.11 |
| $H_2O$ | Karl Fischer's method | 4.64 | 4.74 |

Figure 2:
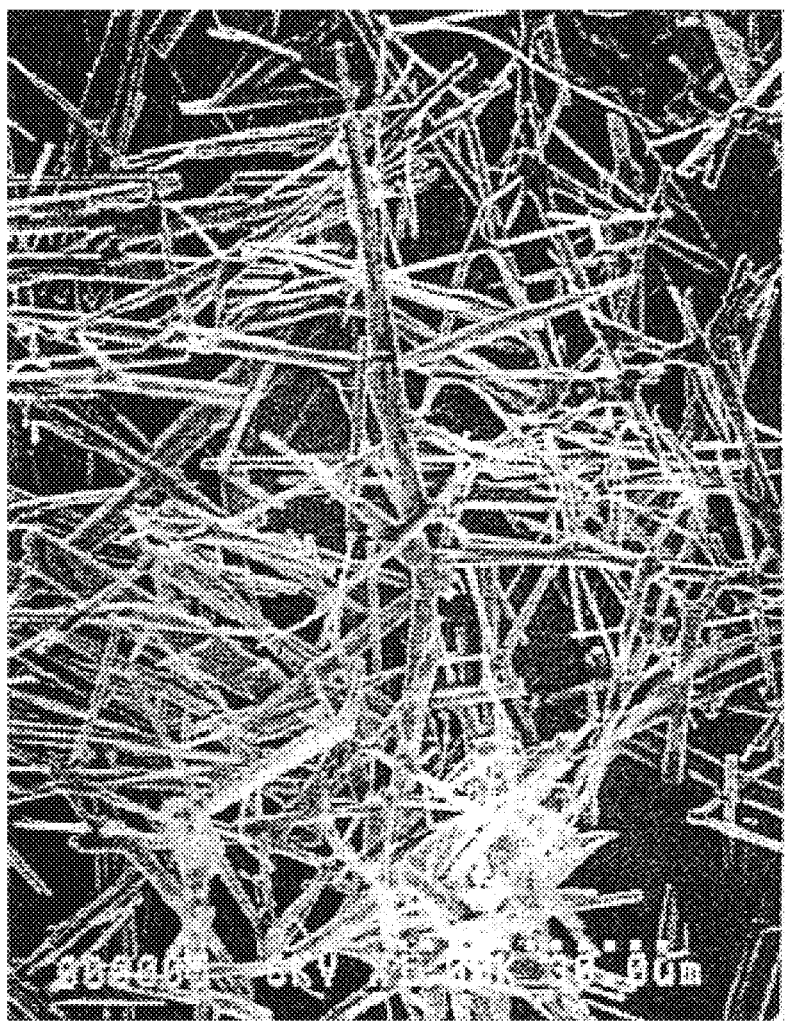
FIG. 2 shows an electron microphotograph (high resolution SEM photograph, ×1,000) of L-ascorbic acid-2-phosphoric acid potassium crystal obtained according to the present invention.
Figure 3:
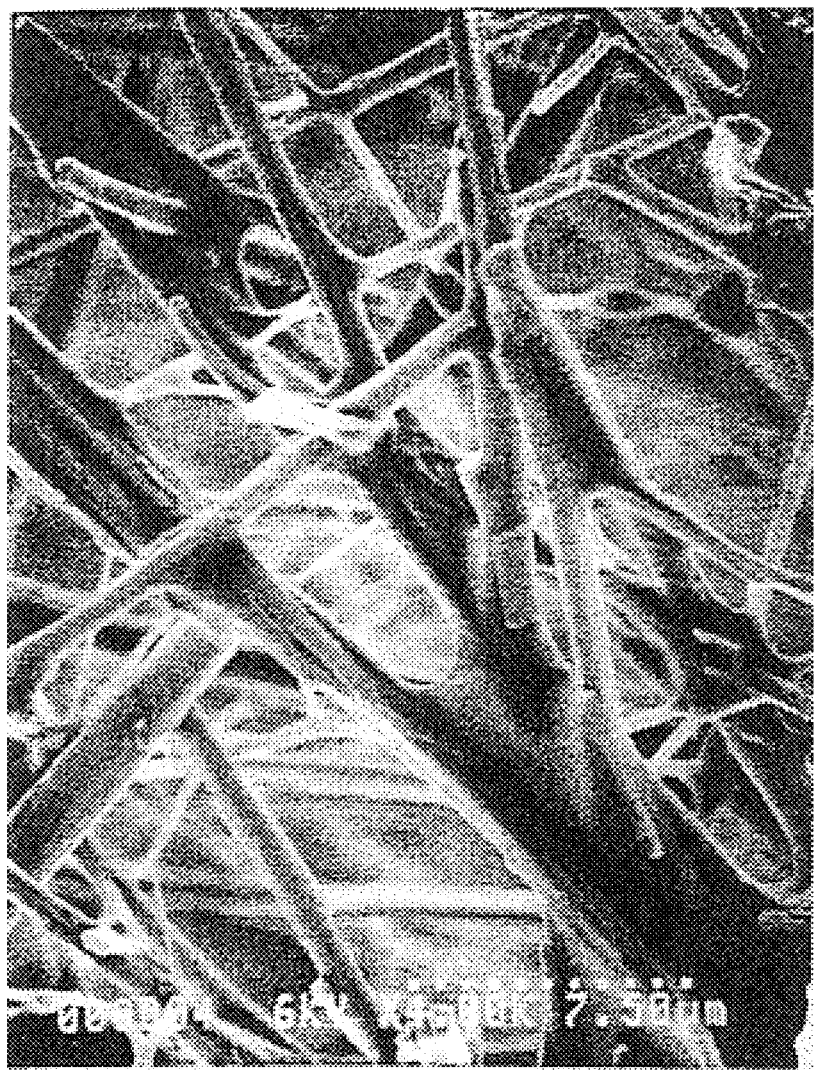
FIG. 3 shows an electron microphotograph (high resolution SEM photograph, ×4,000) of L-ascorbic acid-2-phosphoric acid potassium crystal obtained according to the present invention.

(2) Infrared Ray Absorption Spectrum (Characteristic Absorption (Wavelength) by KBr Method):
  around 3,400 $cm^{-1}$: O—H absorption band
  around 1,600 $cm^{-1}$: absorption band by C=O breathing vibration
  1,000 to 1,200 $cm^{-1}$: P—O absorption band
(3) $^{13}$C-NMR: ($D_2O$, δppm) 179.7, 179.6, 115.4, 81.0, 72.3, 65.3
(4) $^{31}$P-NMR: ($D_2O$, δppm) 2.41
(5) $^1$H-NMR: ($D_2O$, δppm) 4.51 (d, 1H), 4.05 (dt, 1H), 3.75 (d, 2H)
(6) Melting Point (decomposition point): 170–180° C.
(7) X-Ray diffraction spectrum:
  FIG. 1 shows an X-ray diffraction spectrum obtained in the measurement with CuKα ray under conditions of 30 kV and 100 mA.
(8) Crystal Form:
  Usually acicular. FIGS. 2 and 3 each shows an electron microphotograph of crystals.
(9) Solubility:
  Soluble in water (solubility at 25° C. is about 50% (wt/V)) and insoluble in an organic solvent (e.g., alcohols, chloroform).
(10) Stability in Cosmetic Material:
  3 Parts by weight of APK was dissolved in 97 parts by weight of a standard composition lotion shown in Table 2 at a temperature of 25° C. and the change in the deposition of dregs with the time passing was observed at 40° C. for 8 months.

TABLE 2

| Standard Composition Lotion (parts by weight) | |
|---|---|
| 1,3-Butylene glycol | 8.0 |
| Glycerin | 4.0 |
| Ethanol | 3.0 |
| Methyl p-hydroxybenzoate | 0.1 |
| Potassium citrate | 0.5 |
| Potassium edetate | 0.1 |
| Polyoxyethylene hydrogenated castor oil | 0.3 |
| Perfume | 0.1 |
| Hyaluronic acid | 0.1 |
| Purified water | 80.8 |

In the lotion produced using APK crystals, dregs were not deposited even after 8 months.

This reveals that the APK crystal obtained by the production method of the present invention can be suitably used also in preparations (e.g., cosmetic preparations) having a high alcohol concentration, such as lotions.

The APK crystal obtained by the production method of the present invention is highly water-soluble and excellent in the stability, accordingly, the APK crystal can be used not only in cosmetic powder or lotion but also in medical products (e.g., mouth wash, eye drops, bath preparation), cosmetics (e.g., skin lotion, milky lotion, cream, pack), foods (e.g., bread) and animal feedstuff (feedstuff for raising lobster, salmon, yellowtail, eel, carp and the like).

EXAMPLES

The present invention is described in greater detail below by referring to the following Examples, however, the present invention is by no means limited to these Examples. Unless otherwise indicated, all parts, percents, ratios and the like are by weight.

APK having a purity of 99% obtained in the following Examples 1 to 4 exhibited physicochemical properties, appearance and feeling on touch equal to those of the above-described APK crystal.

Example 1

In a nitrogen atmosphere, 1,210 ml of pure water, 303 g of pyridine and 150 g of 5,6-isopropylidene-L-ascorbic acid were mixed and dissolved. The resulting mixed solution was cooled to from 0 to 10° C. and adjusted to a pH of about 13 by adding thereto a 50% aqueous potassium hydroxide solution. To this solution, 150 g of phosphorus oxychloride and a 50% aqueous potassium hydroxide solution were added dropwise and reacted while keeping the pH at 13 and the temperature at from 0 to 10C. After the completion of dropwise addition, pyridine was removed under reduced pressure and 35% hydrochloric acid was added to the residue to adjust the pH to 4.

This solution after the adjustment of the pH was diluted with 6,500 ml of pure water, passed through a column packed with 2,000 ml of a medium basic anion exchange resin (Amberlite IRA-68, produced by organo), and developed with 23.5 L of 0.05N-hydrochloric acid and subsequently with 11 L of 0.2N-hydrochloric acid to obtain a fractional division containing only 2-AP.

To the solution of this fractional separation, a 48% aqueous potassium hydroxide solution was added to adjust the pH to 10. The resulting solution was concentrated under reduced pressure until the APK concentration became 10% (wt/v), thereby obtaining a starting solution.

In a nitrogen atmosphere, 875 ml of 95% methanol was stirred at room temperature at a rate of 380 rpm and thereto 250 ml of the starting solution containing APK was added dropwise over 4 hours. After the completion of dropwise addition, the mixed solution was ripened by further continuing the stirring for one hour. The APK crystals precipitated were collected by filtration using a centrifugal separator and the crystals were thoroughly washed with 100 ml of 95% methanol.

The crystals were vacuum dried at 40° C., as a result, 24.2 g (yield: 91%) of APK having a purity of 99% was obtained.

Example 2

A starting solution containing APK was prepared in the same manner as in Example 1.

In a nitrogen atmosphere, 875 ml of 95% methanol was stirred at a rate of 380 rpm and heated to from 67 to 70° C. While continuing the heating to keep the solution at a temperature of from 67 to 70° C., 250 ml of the starting solution containing APK was added dropwise thereto over a 10 hour period. After the completion of dropwise addition, the mixed solution was ripened by further continuing the stirring for 0.5 hour and then cooled to room temperature over a 4 hour period.

The APK crystals precipitated were collected by filtration using a centrifugal separator and the crystals obtained were thoroughly washed with 150 ml of 95% methanol.

The crystals were vacuum dried at 40° C., as a result, 24.5 g (yield: 92%) of APK having a purity of 99% was obtained.

Example 3

A starting solution containing APK was prepared in the same manner as in Example 1.

In a nitrogen atmosphere, 100 ml of 85% methanol was stirred at room temperature at 380 rpm and thereto 250 ml of the starting solution containing APK was added dropwise at a rate of 0.83 ml/min. At the same time, 800 ml of 95% methanol was added dropwise at a rate of 2.7 ml/min over a 5 hour period. After the completion of dropwise addition, the mixed solution was ripened by further continuing the stirring for one hour.

The APK crystals precipitated were collected by filtration using a centrifugal separator and the solids obtained were thoroughly washed with 100 ml of 95% methanol.

The solids were vacuum dried at 40° C., as a result, 23.7 g (yield: 89%) having a purity of 99% was obtained.

Example 4

32 g of L-ascorbic acid phosphoric acid magnesium was dissolved in 368 g of pure water and the resulting solution was passed through a column packed with 2,000 ml of a strongly acidic cation exchange resin (Amberlite IR-120B, produced by Organo). Further, 1,200 ml of pure water was passed through the column to obtain 1,600 ml of a solution containing only 2-AP. This solution had a magnesium ion content of 3 ml or less.

To this solution, a 48% aqueous potassium hydroxide solution was added to adjust the pH to 10 and convert the 2-AP into APK. The resulting solution was concentrated under reduced pressure until the APK concentration became 12% (wt/V), thereby obtaining a starting solution.

In a nitrogen atmosphere, 400 ml of 95% methanol was stirred at a rate of 380 rpm and cooled to from −5 to 0° C., and thereto, 100 ml of the starting solution containing APK was added dropwise over a 2 hour period. After the completion of dropwise addition, the mixed solution was ripened by further continuing the stirring for 0.25 hour.

The APK crystals precipitated were collected by filtration using a centrifugal separator and the crystals obtained were thoroughly washed with 100 ml of 95% methanol.

The crystals were vacuum dried at 40° C., as a result, 11.5 g (yield: 90%) of APK having a purity of 99% was obtained.

Comparative Example 1

A starting solution containing APK was prepared in the same manner as in Example 1.

In a nitrogen atmosphere, 875 ml of 95% methanol was added dropwise to 250 ml of the solution containing APK at room temperature over a 4 hour period. In 45 minutes after the initiation of dropwise addition, the solution started to become white and turbid, and one hour after the dropwise addition, it was confirmed that glutinous APK was precipitated on the bottom of the container. At the time when the dropwise addition of methanol was completed, the APK was in a glutinous and partly agar-like condition and did not form powder. The supernatant aqueous methanol solution was discarded and the glutinous APK adhering to the bottom of the container was collected by means of a drug spoon and then vacuum dried at 40° C. As a result, 19.4 g of glutinous APK was obtained. The purity by HPLC of this glutinous APK was 90% and the recovery was 70%.

Comparative Example 2

A starting solution containing APK was prepared in the same manner as in Example 4.

In a nitrogen atmosphere, 100 ml of the starting solution containing APK was stirred at a rate of 380 rpm and heated to from 60 to 65° C., and thereto, 200 ml of 98% acetone was added dropwise over 10 minutes while continuing the heating to keep the temperature of from 60 to 65° C. The APK obtained was glutinous and partially agar-like and did not form powder.

By the production method of the present invention, L-ascorbic acid-2-phosphoric acid potassium crystal can be simply produced in a high yield.

The L-ascorbic acid-2-phosphoric acid potassium crystal obtained by the production method of the present invention is used for cosmetic materials, feedstuff, medical products, food additive and the like.

While the invention has been described in detail and with reference to specific embodiments thereof, it will be apparent to one skilled in the art that various changes and modifications can be made therein without departing from the spirit and scope thereof.

What is claimed is:

1. A method for producing an L-ascorbic acid-2-phosphoric acid potassium crystal, comprising adding a solution containing an L-ascorbic acid-2-phosphoric acid potassium to methanol or simultaneously mixing methanol and a solution containing an L-ascorbic acid-2-phosphoric acid potassium, such that methanol accounts for 30% (V/V) or more of the total of said solution and methanol and thereby L-ascorbic acid-2-phosphoic acid potassium is crystallized.

2. The method for producing an L-ascorbic acid-2-phosphoric acid potassium crystal as claimed in claim 1, wherein at the completion of addition of said solution containing L-ascorbic acid-2-phosphoric acid potassium to methanol, methanol accounts for from 30 to 95% (V/V) of the total of said solution and methanol.

3. The method for producing an L-ascorbic acid-2-phosphoric acid potassium crystal as claimed in claim 1, wherein methanol and said solution containing L-ascorbic acid-2-phosphoric acid potassium are simultaneously mixed while keeping the condition such that methanol accounts for from 30 to 95% (V/V) of the total of said solution and methanol.

* * * * *